United States Patent
Yin

(10) Patent No.: US 9,290,710 B2
(45) Date of Patent: Mar. 22, 2016

(54) SYNERGISTIC ANTIMICROBIAL COMPOSITION

(75) Inventor: Bei Yin, Buffalo Grove, IL (US)

(73) Assignee: Dow Global Technologies LLC, Midland, MI (US)

( * ) Notice: Subject to any disclaimer, the term of this patent is extended or adjusted under 35 U.S.C. 154(b) by 974 days.

(21) Appl. No.: 13/500,220

(22) PCT Filed: Oct. 8, 2010

(86) PCT No.: PCT/US2010/052010
§ 371 (c)(1),
(2), (4) Date: Apr. 4, 2012

(87) PCT Pub. No.: WO2011/049761
PCT Pub. Date: Apr. 28, 2011

(65) Prior Publication Data
US 2012/0196836 A1  Aug. 2, 2012

Related U.S. Application Data

(60) Provisional application No. 61/279,397, filed on Oct. 20, 2009.

(51) Int. Cl.
*A01N 57/10* (2006.01)
*A01N 31/08* (2006.01)
*C10L 1/14* (2006.01)
*A01N 57/34* (2006.01)
*C09D 5/14* (2006.01)
*C10L 10/00* (2006.01)
*C10L 1/183* (2006.01)
*C10L 1/185* (2006.01)
*C10L 1/232* (2006.01)
*C10L 1/26* (2006.01)

(52) U.S. Cl.
CPC . *C10L 1/14* (2013.01); *A01N 31/08* (2013.01); *A01N 57/10* (2013.01); *A01N 57/34* (2013.01); *C09D 5/14* (2013.01); *C10L 10/00* (2013.01); *C10L 1/1832* (2013.01); *C10L 1/1855* (2013.01); *C10L 1/232* (2013.01); *C10L 1/2608* (2013.01); *C10L 1/2616* (2013.01); *C10L 1/2625* (2013.01)

(58) Field of Classification Search
CPC ............................ A01N 57/10; A01N 31/08
See application file for complete search history.

(56) References Cited

U.S. PATENT DOCUMENTS

| 3,981,998 | A | 9/1976 | Waldstein |
| 4,978,512 | A | 12/1990 | Dillon |
| 5,094,890 | A | 3/1992 | Smith et al. |
| 5,347,004 | A | 9/1994 | Rivers et al. |
| 5,385,896 | A * | 1/1995 | Bryan et al. .................. 514/129 |
| 5,610,189 | A * | 3/1997 | Whiteley ....................... 514/557 |
| 6,784,168 | B1 | 8/2004 | Jones et al. |
| 8,952,199 | B2 * | 2/2015 | Yin et al. ........................ 568/11 |
| 2004/0234492 | A1 | 11/2004 | Stockel |
| 2005/0158263 | A1* | 7/2005 | Rioux et al. ................. 424/70.1 |
| 2008/0004189 | A1 | 1/2008 | Smith et al. |
| 2008/0234387 | A1* | 9/2008 | Wachtler et al. .............. 514/673 |
| 2010/0298275 | A1 | 11/2010 | Yin et al. |

FOREIGN PATENT DOCUMENTS

| EP | 0385676 | A1 | 9/1990 |
| JP | 11071213 | A | 3/1999 |
| JP | 11222408 | | 8/1999 |
| JP | 3811710 | B2 | 8/2006 |
| JP | 4250676 | B2 | 4/2009 |
| WO | 0004777 | A1 | 2/2000 |

OTHER PUBLICATIONS

EPA, R.E.D. Facts—Dimethoxane: Use Profile and Environmental Fate, May 1996, United State Environmental Protection Agency, printed from http://www.epa.gov/oppsrrd1/reregistration/REDs/factsheets/3064fact.pdf, pp. 1-6.*

Tanaka Y, et al; Industrial antibacterial and bacteriostatic agent-comprising tetrakis(hydroxymethyl)phosphonium salt and further component, useful in e.g. pulp slurry, paint and metal processing oil; WPI Thomson, vol. 1999, No. 21 (Mar. 16, 1999) XP002546071.

Tanaka Y, et al; Industrial bactericide—useful for process water in paper making plant, pulp slurry, cooling water etc.; WPI Thomson, vol. 1999, No. 43 (Aug. 17, 1999), XP002546000.

US Environmental Protection Agency—Office of Pesitcide Programs; Reregistration Eligibility Decision (RED) for Grotan (HHT); (Jun. 27, 2008), pp. 1-38 XP55005609.

"BIOBAN DXN—Material Safety Data Sheet", Dow Product Information, pp. 1-5, XP055024693 (2002).

* cited by examiner

*Primary Examiner* — Gigi Huang
(74) *Attorney, Agent, or Firm* — Kenneth Crimaldi

(57) ABSTRACT

A synergistic antimicrobial composition having two components. The first component is a hydroxymethyl-substituted phosphorus compound. The second component is one of the following biocides: hexahydro-1,3,5-tris(2-hydroxyethyl)-s-triazine, 2,6-dimethyl-1,3-dioxan-4-yl acetate or ortho-phenylphenol or its alkali metal or ammonium salts.

2 Claims, No Drawings

SYNERGISTIC ANTIMICROBIAL COMPOSITION

This invention relates to combinations of biocides, the combinations having greater activity than would be observed for the individual antimicrobial compounds.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, or relatively slow antimicrobial action, or instability under certain conditions such as high temperature and high pH. Combinations of different antimicrobial compounds are sometimes used to provide overall control of microorganisms or to provide the same level of microbial control at lower use rates in a particular end use environment. For example, U.S. Pat. No. 5,385,896 discloses combinations of phosphonium salts and aldehydes, but this reference does not suggest any of the combinations claimed herein. Moreover, there is a need for additional combinations of antimicrobial compounds having enhanced activity to provide effective control of the microorganisms. The problem addressed by this invention is to provide such additional combinations of antimicrobial compounds.

STATEMENT OF THE INVENTION

The present invention is directed to a synergistic antimicrobial composition comprising: (a) a hydroxymethyl-substituted phosphorus compound selected from the group consisting of tetrakis(hydroxymethyl)phoshponium salts and tris(hydroxymethyl)phosphine; and (b) a second biocide selected from the group consisting of (i) hexahydro-1,3,5-tris(2-hydroxyethyl)-s-triazine (HHT); (ii) 2,6-dimethyl-1,3-dioxan-4-yl acetate (DXN); and (iii) ortho-phenylphenol or its alkali metal or ammonium salts; wherein a weight ratio of the hydroxymethyl-substituted phosphorus compound to hexahydro-1,3,5-tris(2-hydroxyethyl)-s-triazine is from 15:1 to 1:15, a weight ratio of the hydroxymethyl-substituted phosphorus compound to 2,6-dimethyl-1,3-dioxan-4-yl acetate is from 15:1 to 1:15, and a weight ratio of the hydroxymethyl-substituted phosphorus compound to ortho-phenylphenol or its alkali metal or ammonium salts is from 15:1 to 1:5.

DETAILED DESCRIPTION OF THE INVENTION

As used herein, the following terms have the designated definitions, unless the context clearly indicates otherwise. The term "antimicrobial compound" refers to a compound capable of inhibiting the growth or propagation of microorganisms, and/or killing microorganisms; antimicrobial compounds include bactericides, bacteristats, fungicides, fungistats, algaecides and algistats, depending on the dose level applied, system conditions and the level of microbial control desired. The term "microorganism" includes, for example, fungi (such as yeast and mold), bacteria and algae. The following abbreviations are used throughout the specification: ppm=parts per million by weight (weight/weight), mL=milliliter, Unless otherwise specified, temperatures are in degrees centigrade (° C.), and references to percentages are by weight (wt %). Percentages of antimicrobial compounds in the composition of this invention are based on the total weight of active ingredients in the composition, i.e., the antimicrobial compounds themselves, exclusive of any amounts of solvents, carriers, dispersants, stabilizers or other materials which may be present. The hydroxymethyl-substituted phosphorus compound is selected from the group consisting of tetrakis(hydroxymethyl)phosphonium salts (e.g., tetrakis(hydroxymethyl)phosphonium sulfate (THPS) and tetrakis(hydroxymethyl)phosphonium chloride) and tris(hydroxymethyl)phosphine. More than one hydroxymethyl-substituted phosphorus compound may be present, in which case the biocide ratio is calculated from the total content of such compounds. Ortho-phenylphenol or its alkali metal or ammonium salts includes lithium, sodium, potassium, rubidium, cesium and ammonium salts. If more than one form of ortho-phenylphenol is present, the biocide ratio is calculated from the total content of such compounds. In some embodiments of the invention, sodium o-phenylphenylate (NaOPP) is used. 2,6-dimethyl-1,3-dioxan-4-yl acetate (DXN) is the same compound as reported in earlier references using the name 6-acetoxy-2,4-dimethyl-m-dioxane.

In some embodiments of the invention, a weight ratio of the hydroxymethyl-substituted phosphorus compound to DXN is from 12:1 to 1:15, alternatively from 12:1 to 1:12, alternatively from 10:1 to 1:12, alternatively from 10:1 to 1:10, alternatively from 9:1 to 1:12, alternatively from 9:1 to 1:10, alternatively from 9:1 to 1:9, alternatively from 8.2:1 to 1:9, alternatively from 8.2:1 to 1:8.2.

In some embodiments of the invention, a weight ratio of the hydroxymethyl-substituted phosphorus compound to ortho-phenylphenol or its alkali metal or ammonium salts is from 12:1 to 1:5, alternatively from 12:1 to 1:4, alternatively from 10:1 to 1:5, alternatively from 10:1 to 1:4, alternatively from 10:1 to 1:3, alternatively from 9:1 to 1:4, alternatively from 9:1 to 1:3, alternatively from 8:1 to 1:3.

In some embodiments of the invention, the antimicrobial composition is substantially free of oxazolidine compounds, i.e, it has less than 5% oxazolidine compounds relative to total biocide active ingredient content, alternatively less than 2%, alternatively less than 1%, alternatively less than 0.5%, alternatively less than 0.1%.

In some embodiments of the invention, the antimicrobial combination of this invention is useful in oil and gas field injection, produced fluids, fracturing fluids and other functional fluids, oil and gas wells, oil and gas operation, separation, storage, and transportation systems, oil and gas pipelines, oil and gas vessels, and fuel. The combination is especially useful in aqueous fluids added to or produced by oil and gas well. The composition also is useful for controlling microorganisms in other industrial water and water containing/contaminated matrixes, such as cooling water, air washer, heat exchangers, boiler water, pulp and paper mill water, other industrial process water, ballast water, wastewater, metalworking fluids, latex, paint, coatings, adhesives, inks, tape joint compounds, pigment, water-based slurries, personal care and household products such as detergent, filtration systems (including reverse osmosis and ultrafiltration systems), toilet bowel, textiles, leather and leather production system, or a system used therewith.

Typically, the amount of the biocide combinations of the present invention to control the growth of microorganisms is from 10 ppm to 5,000 ppm active ingredient. In some embodiments of the invention, the active ingredients of the composition are present in an amount of at least 20 ppm, alternatively at least 50 ppm, alternatively at least 100 ppm, alternatively at least 150 ppm, alternatively at least 200 ppm. In some embodiments, the active ingredients of the composition are present in an amount of no more than 2,000 ppm, alternatively no more than 1,000 ppm, alternatively no more than 500 ppm, alternatively no more than 400 ppm, alternatively no more than 300 ppm, alternatively no more than 250 ppm, alternatively no more than 200 ppm, alternatively no more than 100 ppm, alternatively no more than 50 ppm. Concentrations mentioned above are in a liquid composition containing the biocide combinations. Biocide concentrations in a high-sulfide and high-temperature environment typically will be higher than in other environments. In some embodiments of the invention, active ingredient concentrations downhole in an oil well are from 30 to 500 ppm, alternatively from 50 to 250 ppm. In some embodiments of the invention, active ingredient concentrations for top side treatment at an oil well are from 10 to 300 ppm, alternatively from 30 to 100 ppm.

The present invention also encompasses a method for preventing microbial growth in the use areas described above, especially in oil or natural gas production operations, by incorporating the claimed biocide combination into the materials.

EXAMPLES

Example 1

Synergistic Effect of THPS and HHT Against Sulfate Reducing Bacteria (SRB)

Inside an anaerobic chamber (Bactron anaerobic chamber), a deaerated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of $Na_2SO_4$, 43.92 mg of $Na_2CO_3$ in 1 L water) was contaminated with an oil field isolated anaerobic consortium, mainly SRB, at final bacterial concentrations of $10^6$ to $10^7$ CFU/mL. The aliquots of this contaminated water were then treated with THPS and hexahydro-1,3,5-tris(2-hydroxyethyl)-s-triazine (HHT), or the THPS/HHT combination at different active concentration levels. After the mixtures were incubated at 40° C. for 24 hour, the biocidal efficacy was determined by minimum tested biocide concentration for a complete bacteria kill in the aliquots (MBC). Table 1 summarizes the efficacy of each biocide and their blend, and the Synergy Index*[1] of each combination.

*[1]Synergy Index=Ca/CA+Cb/CB

TABLE 1

Biocidal efficacy of THPS, hexahydro-1,3,5-tris(2-hydroxyethyl)-s-triazine (HHT), THPS/HHT combination, and Synergy Index

| Ratio of THPS to HHT | Average MBC (active ppm) | | Average Synergy Index | p value in Z test*[2] |
|---|---|---|---|---|
| (active w/w) | THPS | HHT | | |
| 1:0 | 6.1 | 0.0 | | |
| 9:1 | 5.2 | 0.6 | 0.88 | 0.00 |
| 3:1 | 5.0 | 1.7 | 0.87 | 0.00 |
| 1:1 | 7.0 | 7.0 | 1.26 | 0.00 |
| 1:3 | 3.3 | 10.0 | 0.69 | 0.00 |
| 1:9 | 2.4 | 21.5 | 0.69 | 0.00 |
| 0:1 | 0.0 | 79.0 | | |

*[2]P value < 0.05 means that there is significant difference between the average Synergy Index and 1.00

Ca: Concentration of biocide A required to achieve a complete bacterial kill when used in combination with Biocide B
CA: Concentration of biocide A required to achieve a complete bacterial kill when used alone
Cb: Concentration of biocide B required to achieve a complete bacterial kill when used in combination with Biocide A
CB: Concentration of biocide B required to achieve a complete bacterial kill when used alone A Synergy Index less than 1 indicates synergy.

Example 2

Evaluation of Biocidal Efficacy of THPS/HHT Combinations, Against Anaerobic Bacteria for a High Temperature and Sulfide-Rich Environment Inside an anaerobic chamber (BACTRON IV), biocides solutions were challenged with $10^4$ to $10^5$ CFU/mL of an oilfield SRB consortium and 10 ppm sulfide ion (added in the form of sodium sulfide). The biocide solutions were then incubated at 80° C. under anaerobic condition for 7 days, with daily challenge of the SRB consortium ($10^4$ to $10^5$ CFU/mL) and sulfide ion (10 ppm). The biocidal efficacy was determined by selecting the lowest testing biocide dosage required for 99.999% or complete bacterial kill after both 2 hours and 7 days of heat, SRB and sulfide exposure. Synergy Index was then calculated. Table 2 summarizes the efficacy of each biocide and their blend, and the Synergy Index of each combination.

TABLE 2

Biocidal efficacy evaluation of THPS, HHT, and THPS/HHT combination for a high temperature and sulfide-rich environment, and Synergy Index

| Ratio of THPS to HHT | Dosage (active ppm) required for 99.999% or complete bacterial kill of both 2 h and 7 day heat, SRB, and sulfide exposure | | Synergy |
|---|---|---|---|
| (active w/w) | THPS | HHT | Index*[3] |
| 1:0 | 88.9 | 0.0 | |
| 5.1:1 | 59.3 | 11.7 | 0.75 |
| 2.3:1 | 59.3 | 26.3 | 0.86 |
| 1:1 | 39.5 | 39.5 | 0.74 |
| 1:2.3 | 17.6 | 39.5 | 0.49 |
| 1:5.1 | 11.7 | 59.3 | 0.58 |
| 0:1 | 0.0 | 133.3 | |

*[3]Synergy Index = Ca/CA + Cb/CB
Ca: Concentration of biocide A required to achieve a 99.999% bacterial kill when used in combination with Biocide B
CA: Concentration of biocide A required to achieve a 99.999% bacterial kill when used alone
Cb: Concentration of biocide B required to achieve a 99.999% bacterial kill when used in combination with Biocide A
CB: Concentration of biocide B required to achieve a 99.999% bacterial kill when used alone A Synergy Index less than 1 indicates synergy.

The data above show that the THPS and HHT combination was synergistic for a high temperature and sulfide-rich environment.

Example 3

Synergistic Effect of THPS and DXN, Against Sulfate Reducing Bacteria (SRB)

Inside an anaerobic chamber (Bactron III), a deaerated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of $Na_2SO_4$, 43.92 mg of $Na_2CO_3$ in 1 L water) was contaminated with an oil field isolated anaerobic SRB consortium at final bacterial concentrations of $10^6$ to $10^7$ CFU/mL. The aliquots of this contaminated water were then treated with THPS, DXN, or the THPS/DXN combinations at different active concentration levels. After the mixtures were incubated at 40° C. for 24 hour, the viable bacterial number were enumerated using a serial dilution method and the biocidal efficacy was determined by the biocide dosage required for 99.99% bacterial reduction in 24 hours. Synergy Index was then calculated. Table 3 summarizes the efficacy of each biocide and their blends, and the Synergy Index of each combination.

TABLE 3

Biocidal efficacy of THPS, DXN, THPS/DXN combination, and Synergy Index

| Ratio of THPS to DXN | Dosage required for 99.99% bacterial reduction (active ppm) | | Synergy Index*4 |
|---|---|---|---|
| (active w/w) | THPS | DXN | |
| 1:0 | 5.5 | 0.0 | |
| 8.2:1 | 4.2 | 0.5 | 0.76 |
| 2.9:1 | 4.2 | 1.5 | 0.77 |
| 1:1 | 4.2 | 4.2 | 0.77 |
| 1:2.9 | 3.2 | 9.2 | 0.62 |
| 1:8.2 | 3.2 | 26.4 | 0.67 |
| 0:1 | 0.0 | 330.9 | |

*4Synergy Index = Ca/CA + Cb/CB
Ca: Concentration of biocide A required to achieve a 99.99% bacterial kill when used in combination with Biocide B
CA: Concentration of biocide A required to achieve a 99.99% bacterial kill when used alone
Cb: Concentration of biocide B required to achieve a 99.99% bacterial kill when used in combination with Biocide A
CB: Concentration of biocide B required to achieve a 99.99% bacterial kill when used alone A Synergy Index less than 1 indicates synergy.

Example 4

Synergistic Effect of THPS and NaOPP, Against Sulfate Reducing Bacteria (SRB)

Inside an anaerobic chamber (Bactron anaerobic chamber), a deaerated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of $Na_2SO_4$, 43.92 mg of $Na_2CO_3$ in 1 L water) was contaminated with an oil field isolated SRB consortium, at final bacterial concentrations of $10^6$ to $10^7$ CFU/mL. The aliquots of this contaminated water were then treated with THPS, NaOPP, or the THPS/NaOPP combinations at different active concentration levels. After the mixtures were incubated at 40° C. for 24 hours, the viable bacteria in the aliquots were detected in culture medium. The biocidal efficacy was determined by minimum tested biocide concentration for a complete bacterial kill in the aliquots (MBC). Table 4 summarizes the efficacy of each biocide and their blends, and the Synergy Index of each combination.

TABLE 4

Biocidal efficacy of THPS, NaOPP, THPS/NaOPP combination, against anaerobic bacteria

| Ratio of THPS to NaOPP | Average MBC (active ppm) | | Average Synergy Index*1 | p value*2 in z test |
|---|---|---|---|---|
| (active w/w) | THPS | NaOPP | | |
| 1:0 | 7.9 | 0.0 | | |
| 9:1 | 6.1 | 0.7 | 0.77 | 0.04 |
| 3:1 | 5.1 | 1.7 | 0.66 | 0.00 |
| 1:1 | 8.5 | 8.5 | 1.10 | 0.51 |
| 1:3 | 6.4 | 19.1 | 0.86 | 0.00 |
| 1:9 | 6.1 | 55.1 | 0.94 | 0.62 |
| 0:1 | 0.0 | 333.3 | | |

Example 5

Synergistic Effect of THPS and NaOPP, Against Sulfate Reducing Bacteria (SRB)

Inside an anaerobic chamber (Bactron anaerobic chamber), a deaerated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of $Na_2SO_4$, 43.92 mg of $Na_2CO_3$ in 1 L water) was contaminated with an oil field isolated anaerobic consortium, mainly SRB, at final bacterial concentrations of $10^7$ CFU/mL. The aliquots of this contaminated water were then treated with THPS, NaOPP, or the THPS/NaOPP combinations at different active concentration levels. After the mixtures were incubated at 40° C. for 24 hour, the viable bacteria were enumerated using serial dilution method. The biocidal efficacy was determined by minimum tested biocide concentration for 99.999% bacterial reduction in the aliquots. Table 5 summarizes the efficacy of each biocide and their blends, and the Synergy Index of each combination.

TABLE 5

Biocidal efficacy of THPS, NaOPP, THPS/NaOPP combination, against anaerobic bacteria

| Ratio of THPS to NaOPP | Concentration (ppm active) required for 99.999% bacterial reduction | | Synergy Index*3 |
|---|---|---|---|
| (active w/w) | THPS | NaOPP | |
| 1:0 | 11.9 | 0.0 | |
| 2.25:1 | 7.9 | 3.5 | 0.68 |
| 1:1 | 7.9 | 7.9 | 0.69 |
| 1:2.25 | 7.9 | 17.8 | 0.72 |
| 1:5.06 | 11.9 | 60.0 | 1.19 |
| 1:7.59 | 7.9 | 60.0 | 0.86 |
| 0:1 | 0.0 | 303.8 | |

Example 6

Synergistic Effect of THPS and NaOPP, Against Aerobic Bacteria

A PBS buffer (pH7) was contaminated with *Psedomonas aeruginosa* ATCC 10145 and *Staphylococcus aureus* ATCC 6538 at final bacterial concentration of $-10^6$ CFU/ml. The aliquots of this contaminated water were then treated with THPS, NaOPP, or the THPS/NaOPP combinations at different active concentration levels. After the mixtures were incubated at 37° C. for 24 hour, the viable bacteria were enumerated using serial dilution method. The biocidal efficacy was determined by minimum tested biocide concentration for 99.999% bacterial reduction in the aliquots. Table 6 summarizes the efficacy of each biocide and their blends, and the Synergy Index of each combination.

TABLE 6

Biocidal efficacy of THPS, NaOPP, THPS/NaOPP combination, against aerobic bacteria

| Ratio of THPS to NaOPP (active w/w) | Concentration (ppm active) required for 99.999% bacterial reduction | | Synergy Index*[3] |
|---|---|---|---|
| | THPS | NaOPP | |
| 1:0 | 26.7 | 0.0 | |
| 2.25:1 | 17.8 | 7.9 | 0.70 |
| 1:1 | 17.8 | 17.8 | 0.75 |
| 1:2.25 | 17.8 | 40.0 | 0.86 |
| 1:5.06 | 17.8 | 90.0 | 1.11 |
| 1:7.59 | 17.8 | 135.0 | 1.33 |
| 0:1 | 0.0 | 202.5 | |

As shown in Tables 4 to 6, THPS in combination with NaOPP showed a synergistic effect and much lower dosages were needed for good SRB control when used in combination.

The invention claimed is:

1. A synergistic antimicrobial composition comprising: (a) tetrakis(hydroxymethyl)phosphonium sulfate; and (b) a second biocide which is ortho-phenylphenol or its alkali metal or ammonium salts; wherein a weight ratio of tetrakis(hydroxymethyl)phosphonium sulfate to ortho-phenylphenol or its alkali metal or ammonium salts is from 9:1 to 3:1 or 2.25:1 to 1:2.25.

2. The composition of claim 1 in which the second biocide is a sodium salt of ortho-phenylphenol.

* * * * *